United States Patent
Kell et al.

(10) Patent No.: US 8,536,544 B2
(45) Date of Patent: Sep. 17, 2013

(54) APPARATUS AND A METHOD OF DETERMINING THE PRESENCE OF AN ALUMINA LAYER ON A SURFACE OF A COMPONENT

(75) Inventors: James Kell, Nottingham (GB); John C. C. Day, Bristol (GB)

(73) Assignee: Rolls-Royce PLC, London (GB)

( * ) Notice: Subject to any disclaimer, the term of this patent is extended or adjusted under 35 U.S.C. 154(b) by 307 days.

(21) Appl. No.: 12/970,110

(22) Filed: Dec. 16, 2010

(65) Prior Publication Data

US 2011/0180727 A1    Jul. 28, 2011

(30) Foreign Application Priority Data

Jan. 28, 2010 (GB) .................... 1001354.8

(51) Int. Cl.
*G01J 1/58* (2006.01)
*G01B 15/02* (2006.01)
*C23C 14/54* (2006.01)

(52) U.S. Cl.
USPC .............................. 250/459.1; 378/50; 427/9

(58) Field of Classification Search
USPC .................... 250/458.1, 459.1, 492.3; 427/9; 378/50
See application file for complete search history.

(56) References Cited

U.S. PATENT DOCUMENTS

| | | | |
|---|---|---|---|
| 4,679,938 A * | 7/1987 | Flamholz | 356/237.2 |
| 4,774,150 A | 9/1988 | Amano et al. | |
| 6,153,889 A * | 11/2000 | Jones | 250/559.45 |
| 6,974,641 B1 * | 12/2005 | Choy et al. | 428/704 |
| 2003/0115941 A1 | 6/2003 | Srivastava et al. | |
| 2005/0073673 A1 | 4/2005 | Devitt et al. | |
| 2008/0305244 A1 | 12/2008 | Cui et al. | |

FOREIGN PATENT DOCUMENTS

| | | |
|---|---|---|
| DE | 102 17 950 A1 | 11/2002 |
| DE | 10 2006 052 114 A1 | 5/2008 |
| EP | 1 016 862 A1 | 7/2000 |
| GB | 2 455 850 A | 6/2009 |
| JP | A-2006-2223 | 1/2006 |

OTHER PUBLICATIONS

Horiba, "Raman Scattering and Fluorescence," Dec. 9, 2006, pp. 1-2.
"Raman scattering," *Wikipedia*, Nov. 23, 2007, http://en.Wikipedia.org/wiki/Raman_scattering, pp. 1-5.
Sovany et al., "Raman spectroscopic investigation of film thickness," *Polymer Testing*, vol. 28, 2009, pp. 770-772.
Stiles et al., "Surface-Enhanced Raman Spectroscopy," *Annual Review of Analytical Chemistry*, Mar. 18, 2008, vol. 2008.1, pp. 601-626.

(Continued)

*Primary Examiner* — David Porta
*Assistant Examiner* — Faye Boosalis
(74) *Attorney, Agent, or Firm* — Oliff & Berridge, PLC

(57) ABSTRACT

Provided is a method for determining the presence of an alumina layer on a surface of a component. The method includes illuminating a surface of a component with radiation; detecting radiation emitted at a particular wavelength; analyzing the detected radiation; to determine the thickness of the alumina at at least one point on the surface of the component; and comparing the determined thickness of the alumina at the at least one point on the surface of the component with a predetermined thickness of alumina at that point to decide if the thickness of alumina at the at least one point on the surface of the component is satisfactory.

27 Claims, 2 Drawing Sheets

(56) References Cited

OTHER PUBLICATIONS

Search Report issued in European Application No. 10 19 5244 dated Feb. 14, 2011.

British Search Report dated Feb. 25, 2010 in British Patent Application No. GB1001354.8.

\* cited by examiner

APPARATUS AND A METHOD OF DETERMINING THE PRESENCE OF AN ALUMINA LAYER ON A SURFACE OF A COMPONENT

The present invention relates to an apparatus and a method of determining the presence of an alumina layer on a surface of a component, and particularly relates to an apparatus and a method of determining the presence of an alumina layer on a surface of a gas turbine engine component, for example a turbine blade, a turbine vane or a combustor component.

Components of a gas turbine engine which are subjected to corrosive conditions are provided with protective coatings to inhibit corrosion of the components. One family of protective coatings uses aluminising to form an aluminium rich coating on the surface of the component, such coatings may be simple aluminide coatings, platinum aluminide coatings, chromium aluminide coatings or silicon aluminide coatings etc. These aluminium rich coatings produce a protective layer of alumina.

The aluminium and alumina coated components of the gas turbine engine are inspected to check that the components have been provided with the aluminium rich coating and alumina layer on all those surfaces which require the aluminium rich coating and alumina layer. The current method of inspecting the aluminium and alumina coated components of the gas turbine engine uses a "heat tint". A "heat tint" comprises cleaning the component, degreasing the component, cleaning the component, grit blasting the component, cleaning the component, placing the component in a furnace for 1 hour and inspecting the component by eye.

A problem with the "heat tint" is that it is time consuming and requires many processes before the inspection may be made and each component given a "heat tint" is individually inspected by an operator making the inspection process highly subjective.

Accordingly the present invention seeks to provide a novel apparatus and method of determining the presence of an alumina layer on a surface of a component which reduces, preferably overcomes, the above mentioned problems.

Accordingly the present invention provides an apparatus for determining the presence of an alumina layer on a surface of a component, an aluminium containing layer being arranged on the surface of the component and an alumina layer being arranged on the aluminium containing layer, the apparatus comprising means to directly illuminate a surface of a component with radiation at a suitable wavelength to produce excitation of electrons from a normal energy state to a higher energy state in any alumina on the surface of the component, means to detect radiation emitted at a particular wavelength by electrons reverting from the higher energy state to the normal energy state in any alumina on the surface of the component, means to analyse the radiation emitted by electrons reverting from the higher energy state to the normal energy state in any alumina on the surface of the component to determine the thickness of the alumina at at least one point on the surface of the component and means to compare the determined thickness of the alumina at the at least one point on the surface of the component with a predetermined thickness of alumina at that point on the surface of the component to decide if the thickness of alumina at the at least one point on the surface of the component is satisfactory.

Preferably the means to analyse the radiation emitted by electrons reverting from the higher energy state to the normal energy state in any alumina on the surface of the component is arranged to determine the thickness of the alumina at a plurality of points on the surface of the component and the means to compare the determined thickness of the alumina is arranged to compare the determined thickness at each of the plurality of points on the surface of the component with a predetermined thickness of alumina at each of the plurality of points on the surface of the component to decide if the thickness of alumina at each of the plurality of points on the surface of the component is satisfactory.

Preferably the means to analyse the radiation emitted by electrons reverting from the higher energy state to the normal energy state in any alumina on the surface of the component is arranged to determine the thickness of the alumina at each point on the surface of the component and the means to compare the determined thickness of the alumina is arranged to compare the determined thickness at each point on the surface of the component with a predetermined thickness of alumina at that point on the surface of the component to decide if the thickness of alumina at each point on the surface of the component is satisfactory.

Preferably the means to illuminate the surface of the component is arranged to illuminate the surface of the component with ultraviolet radiation, radiation in the blue region and/or radiation in the green region of the radiation spectrum. Preferably the means to illuminate the surface of the component is arranged to illuminate the surface of the component with radiation at wavelength of 488 nm, 505 nm, 514 nm or 530 nm. Preferably the means to detect radiation is arranged to detect radiation at a wavelength of 692 nm to 696 nm. Preferably the means to illuminate the surface of the component with radiation comprises at least one light emitting diode or at least one laser. Preferably the means to detect radiation comprises a camera. Preferably the camera is a CCD camera or a CMOS camera. Preferably the means to analyse and compare comprises a personal computer. Preferably the means to illuminate the surface of the component comprises a plurality of light emitting diodes arranged in an array around the camera. Preferably the camera has a red band-pass filter. Preferably the at least one light emitting diode has a green short-pass filter, a blue filter, an ultraviolet filter or a short pass filter which blocks red light.

Preferably the apparatus comprises a radiation tight enclosure and the means to illuminate the surface of the component is arranged to illuminate an external surface of the component and the means to illuminate the surface of the component and the means to detect radiation are arranged in the light tight enclosure. Alternatively, the apparatus comprises a boroscope to illuminate an internal surface of the component.

The present invention also provides a method of determining the presence of an alumina layer on a surface of a component, an aluminium containing layer being arranged on the surface of the component and an alumina layer being arranged on the aluminium containing layer, the method comprising the steps of:— a) directly illuminating a surface of a component with radiation at a suitable wavelength to produce excitation of electrons from a normal energy state to a higher energy state in any alumina on the surface of the component, b) detecting radiation emitted at a particular wavelength by electrons reverting from the higher energy state to the normal energy state in any alumina on the surface of the component, c) analysing the radiation emitted by electrons reverting from the higher energy state to the normal energy state in any alumina on the surface of the component to determine the thickness of the alumina at at least one point on the surface of the component, d) comparing the determined thickness of the alumina at the at least one point on the surface of the component with a predetermined thickness of alumina at that point on the surface of the component to decide if the thickness of alumina at the at least one point on the surface of the component is satisfactory.

Preferably step c) comprises analysing the radiation emitted by electrons reverting from the higher energy state to the normal energy state in any alumina on the surface of the component to determine the thickness of the alumina at a plurality of points on the surface of the component and step d) comprises comparing the determined thickness of the alumina at each of the plurality of points on the surface of the component with a predetermined thickness of alumina at each of the plurality of points on the surface of the component to decide if the thickness of alumina at each of the plurality of points on the surface of the component is satisfactory.

Preferably step c) comprises analysing the radiation emitted by electrons reverting from the higher energy state to the normal energy state in any alumina on the surface of the component to determine the thickness of the alumina at each point on the surface of the component and step d) comprises comparing the determined thickness of the alumina at each point on the surface of the component with a predetermined thickness of alumina at that point on the surface of the component to decide if the thickness of alumina at each point on the surface of the component is satisfactory.

Preferably the suitable wavelength is ultraviolet radiation, radiation in the blue region and/or radiation in the green region of the radiation spectrum. Preferably the suitable wavelength is 488 nm, 505 nm, 514 nm or 530 nm. Preferably the particular wavelength is 692 nm to 696 nm. Preferably step a) comprises illuminating the surface of the component with radiation from at least one light emitting diode or radiation from at least one laser. Preferably step b) comprises detecting radiation with a camera. Preferably the camera is a CCD camera or a CMOS camera. Preferably step c) and step d) comprise analysing and comparing using a personal computer. Preferably a plurality of light emitting diodes are arranged in an array around the camera. Preferably the camera has a red band-pass filter. Preferably the at least one light emitting diode has a green short-pass filter, a blue filter, an ultraviolet filter or a short pass filter which blocks red light.

Preferably the method comprises placing the component in a radiation tight enclosure and illuminating an external surface of the component. Alternatively, the method comprises inserting a boroscope into the component and illuminating an internal surface of the component.

Preferably the component is a component of a gas turbine engine.

Preferably the component is a turbine blade or a turbine vane.

Preferably the alumina layer is arranged on an aluminium containing layer on the component.

Preferably the aluminium containing layer is an aluminide layer, a platinum aluminide layer, a silicon aluminide layer, a chromium aluminide layer or a MCrAlY layer, where M is nickel, cobalt or a combination of nickel and cobalt, Cr is chromium, Al is aluminium and Y is yttrium.

The present invention will be more fully described by way of example with reference to the accompanying drawings, in which:—

Figure 1:
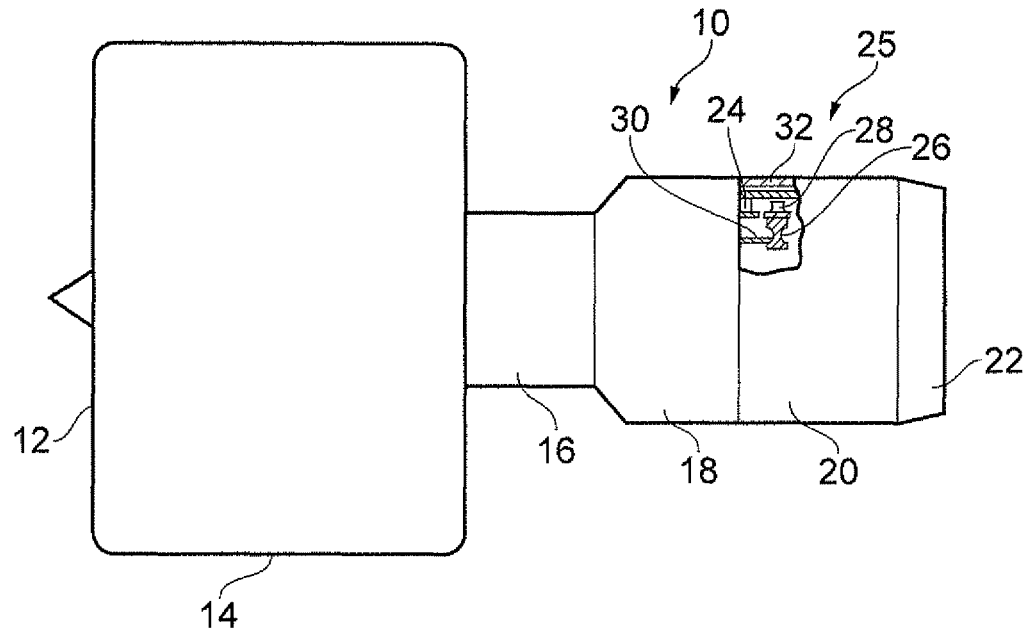
FIG. 1 is a partially cut-away view of a turbofan gas turbine engine showing a component having an alumina layer.

A turbofan gas turbine engine 10, as shown in FIG. 1, comprises in flow series an inlet 12, a fan section 14, a compressor section 16, a combustion section 18, a turbine section 20 and an exhaust 22. The fan section 14 comprises a fan (not shown). The compressor section 16 comprises in flow series an intermediate-pressure compressor (not shown) and a high-pressure compressor (not shown). The turbine section 20 comprises in flow series a high-pressure turbine 25, an intermediate-pressure turbine (not shown) and a low-pressure turbine (not shown). The low-pressure turbine is arranged to drive the fan via a first shaft, the intermediate-pressure turbine is arranged to drive the intermediate-pressure compressor via a second shaft and the high-pressure turbine 25 is arranged to drive the high-pressure compressor via a third shaft 30. The high-pressure turbine 25 comprises a turbine disc 26, which carries a plurality of circumferentially spaced radially outwardly extending turbine rotor blades 28. A plurality of nozzle guide vanes 24 are arranged upstream of the turbine rotor blades 28 to direct hot gases from the combustion section 18 onto the turbine rotor blades 28. An outer turbine casing 32 is provided around the turbines.

Figure 5:
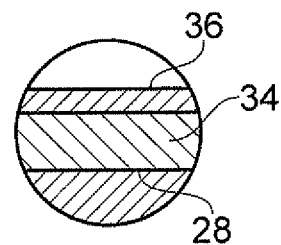
FIG. 5 is a cross-sectional view through a portion of a component showing the alumina layer.

The turbine rotor blades 28 are provided with a protective coating 34 to inhibit corrosion of the turbine rotor blades 28, as shown in FIG. 5. The protective coating 34 may be a simple aluminide coating, a platinum aluminide coating, a chromium aluminide coating or a silicon aluminide coating or a MCrAlY coating, where M is nickel, cobalt, iron or a combination of any two or more of these elements, Cr is chromium, Al is aluminium and Y is yttrium. These aluminium containing coatings, or aluminium rich coatings, produce a protective layer of alumina 36. The protective coating 34 may be applied only on those surfaces of the turbine rotor blade 28 subject to corrosion, for example the protective coating 34 may be applied to the surface of one or more of the aerofoil portion 29, the platform portion 31, the shank portion 33 and the cooling passages within the turbine rotor blade 28. The protective coating 34 may be different at different regions of the surface of the turbine rotor blade 28, for example the protective coating 34 on the surface of the aerofoil portion 29 and the platform portion 31 may be different to the protective coating 34 on the surface of the cooling passages and shank portion 33. The root portion 35 does not have a protective coating.

Figure 2:
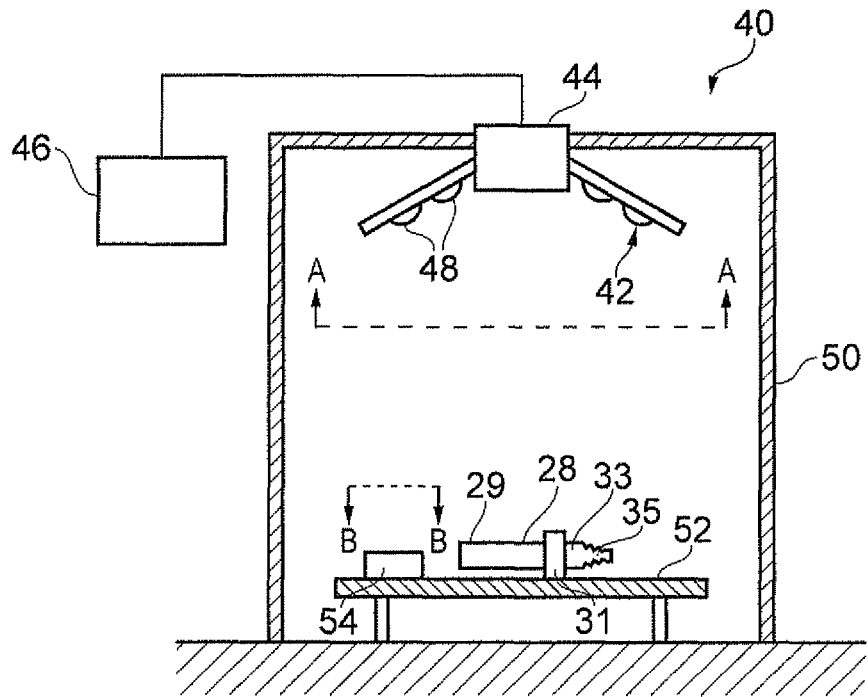
FIG. 2 is a cross-sectional view through an apparatus for determining the presence of an alumina layer on a component according to the present invention.
Figure 3:
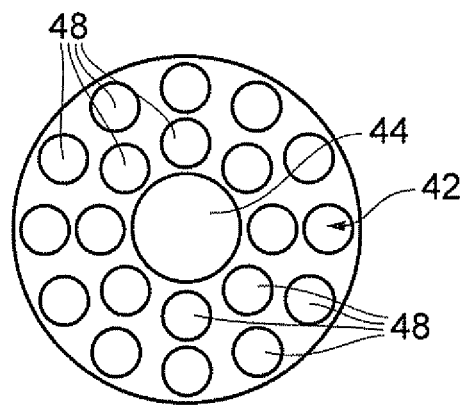
FIG. 3 is a view looking in the direction of arrow A in FIG. 2.
Figure 4:
FIG. 4 is a view looking in the direction of arrow B in FIG. 2.

In order to determine the presence of the alumina 36 and hence the aluminium rich coating 34 on a surface of a component 28 an apparatus 40 as shown in FIGS. 2 to 4 is used. The apparatus 40 for determining the presence of an alumina layer 36 on a component 28, e.g. a turbine rotor blade, comprises means 42 to illuminate a surface of the component 28, with radiation at a suitable wavelength to produce excitation of electrons from a normal energy state to a higher energy state in any alumina 36 on the surface of the component 28. The apparatus 40 comprises means 44 to detect radiation emitted at a particular wavelength by electrons reverting from the higher energy state to the normal energy state in any alumina 36 on the surface of the component 28. The apparatus 40 comprises means 46 to analyse the radiation emitted by electrons reverting from the higher energy state to the normal energy state in any alumina 36 on the surface of the component 28 to determine the thickness of the alumina 36 at at least one point on the surface of the component 28 and the apparatus 40 also comprises means 46 to compare the determined thickness of the alumina 36 at the at least one point on the surface of the component 28 with a predetermined thickness of alumina 36 at that point on the surface of the component 28 to decide if the thickness of alumina 36 at the at least one point on the surface of the component 28 is satisfactory.

The means 46 to analyse the radiation emitted by electrons reverting from the higher energy state to the normal energy state in any alumina 36 on the surface of the component 28 is arranged to determine the thickness of the alumina 36 at a plurality of points on the surface of the component 28 and the means 46 to compare the determined thickness of the alumina 36 is arranged to compare the determined thickness at each of the plurality of points on the surface of the component 28 with a predetermined thickness of alumina 36 at each of the plurality of points on the surface of the component 28 to decide if the thickness of alumina 36 at each of the plurality of points on the surface of the component 28 is satisfactory.

The means 46 to analyse the radiation emitted by electrons reverting from the higher energy state to the normal energy state in any alumina 36 on the surface of the component 28 may be arranged to determine the thickness of the alumina 36 at each point on the surface of the component 28 and the means 46 to compare the determined thickness of the alumina 36 is arranged to compare the determined thickness at each point on the surface of the component 28 with a predetermined thickness of alumina 36 at that point on the surface of the component 28 to decide if the thickness of alumina 36 at each point on the surface of the component 28 is satisfactory.

As shown in FIGS. 2 and 3 the means 42 to illuminate the surface of the component 28 is arranged to illuminate the surface of the component 28 with radiation at wavelength of 505 nm. The means 42 to illuminate the surface of the component 28 with radiation comprises at least one light emitting diode 48. The at least one light emitting diode may be a cyan high intensity light emitting diode. The cyan light emitting diodes emit a lot of radiation over the whole of the green and blue region, and produce a peak at 505 nm, but emit little radiation in the red region. It may be possible to use at least one laser emitting radiation at a suitable wavelength as the excitation source instead of the light emitting diodes. The means 44 to detect radiation is arranged to detect radiation at a wavelength of 692 nm to 696 nm. The means 44 to detect radiation comprises a camera and the camera is a CCD camera or a CMOS camera. As shown in FIGS. 2 and 3 the plurality of light emitting diodes 48 are arranged in an array. The array of light emitting diodes 48 is arranged around the camera 44. The particular array of light emitting diodes 48 comprises twelve LEDs 48 arranged in an outer ring around the camera 44 and six, eight, or more, LEDs 48 arranged in an inner ring around the camera. Other suitable arrays of LEDs 48 may be used. The camera 44 has a red band-pass filter placed over the lens of the camera 44 to allow radiation of the fluorescent wavelength, 695 nm +/−5 nm, to pass therethrough. The at least one light emitting diode 48 has a green short-pass filter placed over the radiation source to remove any residual component of the fluorescent wavelength.

The apparatus 40 comprises a radiation tight enclosure 50 and the means 42 to illuminate the surface of the component 28 is arranged to illuminate an external surface of the component 28 and the means 42 to illuminate the surface of the component 28 and the means 44 to detect radiation are arranged in the light tight enclosure 50. The apparatus 40 comprises a worktable 52 arranged in the light tight enclosure 50 and the component 28 to be inspected is placed upon the worktable 52 and a graticule and a piece of fluorescent material 54, e.g. sapphire, with a standard graduated neutral density filter is placed on the surface of the fluorescent material illuminated by the radiation. Alternatively, the apparatus may comprise a boroscope to illuminate an internal surface of the component so that an alumina layer and aluminium containing coating on the internal surface of a cooling passage within the turbine rotor blade may be inspected.

Preferably the means 46 to analyse and compare comprises a personal computer, PC.

In operation, in order to determine if a component 28 has sufficient thickness of an alumina layer 36 and hence a sufficient thickness of a protective coating 34, the component 28 is placed on the worktable 52 in the light tight enclosure 50. The light emitting diodes 48 illuminate the surface of the component 28 with radiation at a wavelength of about 505 nm and the camera 44 detects radiation at a wavelength of 692 nm to 696 nm. In alumina electrons reverting from the higher energy state to the normal energy state emit radiation at a peak wavelength of 694 nm, but the peak wavelength actually covers a range of 692 nm to 696 nm. The camera 44 takes still images of the surface of the component 28 before and after illumination by the light emitting diodes 48 and the PC 46 analyses the still images of the surface of the component 28 using image analysis software. The fluorescent material 54 is also illuminated by the light emitting diodes 48 and the graduated neutral density filter provides a calibration for direct comparison between two different components or direct comparison between exposures taken under different levels of illumination. The PC 46 determines from the images taken by the camera 44 the thickness of the alumina 36 at all points on the surface of the component 28 and then compares the measured thickness of the alumina 36 at all points on the surface of the component 28 with predetermined thicknesses of alumina 36 at all points on the surface of the component 28 to decide if the thickness of alumina 36 at all the points on the surface of the component 28 is satisfactory. Thus, the PC analyses each pixel of the image of the component 28, taken by the camera 44, and measures the intensity of the fluorescence at each pixel of the image of the component 28 and the intensity of the fluorescence at each pixel of the image of the component 28 correlates to the thickness of the alumina layer 36 at that point of the component 28. The measured thickness of the alumina 36 at each pixel/point on the component 28 is compared to a predetermined required thickness of alumina 36 at that point on the surface of the component 28. The component 28 is then turned over and the opposite surface of the component 28 is inspected.

The alumina 36 on the protective coating 34, aluminium containing coating, on the surface of the component 28 is illuminated directly by the radiation emitted by the means 42 to illuminate the surface of the component 28 because there are no intervening coatings, or layers, on top of the alumina 36 on the protective coating 34, aluminium containing coating.

If it is determined that the thickness of the alumina 36 and hence the thickness of the protective coating 34, the aluminium containing coating, is insufficient the component 28 may be coated with more of the aluminium containing coating to increase the thickness of the protective coating 34 and hence increase the thickness of the alumina 36.

Although the present invention has been described with reference to illuminating the surface of the component with radiation at wavelength of 505 nm, in practice it is possible to use any wavelength shorter than the wavelength of the radiation emitted by the electrons falling form the higher energy state to a normal energy state in the alumina, e.g. less than a wavelength of 690 nm to 700 nm. Thus, it may be possible to use light emitting diodes emitting radiation with ultraviolet wavelengths. In the case where one or more lasers are used, e.g. when used with a horoscope, argon ion lasers with wavelengths of 514 nm and 488 nm may be used, diode lasers with wavelengths of 530 nm may be used, ultraviolet, blue or green lasers with good intensity may be used. Thus the suitable wavelength is ultraviolet radiation, radiation in the blue region and/or radiation in the green region of the radiation spectrum.

Although the present invention has been described with reference to a fixed bandpass filter in front of the camera, it is possible to use a tunable filter in front of the camera. The advantage of using a tunable filter is that this allows hyper spectral imaging in order to look for shifts in the peak wavelength of emission of alumina. The shifts in the peak wavelength of emission of alumina are due to strains, or changes in the strain, in the alumina. Detecting changes in the peak wavelength of emission of the alumina would enable the strain at different positions in the alumina coating to be detected and mapped.

Although the present invention has been described with reference to the use of a green short pass filter in front of the light emitting diodes, it may be possible to use any filter which passes as much radiation as possible at wavelengths below the wavelength of the radiation being detected and block as much as possible of the radiation in the wavelengths being detected. Thus, the filter should pass blue and ultraviolet. Thus, a short pass filter which blocks red light may be used.

The advantage of the present invention is that quantitative data is derived from the component quickly and easily and the present invention enables an indication of whether an alumina coating and hence an aluminium containing coating is present on all those surfaces which require the aluminium containing coating, or aluminium rich coating, and alumina layer, The present invention requires only minimal cleaning of the component and does not require any grit blasting of the component or placing of the component in a furnace. The present invention allows inspection of the whole of the surface of the component in a single exposure to the radiation. The graduated neutral density filter on top of the fluorescent material allows a reference to be taken with each exposure and this allows direct comparison of images taken using different exposure parameters, e.g. different illumination levels.

Although the present invention has been described with reference to the component being a turbine blade, the component may be any component of a gas turbine engine, e.g. a turbine vane, a combustor component or any other component having an alumina layer.

The alumina layer may be arranged on an aluminium containing coating on the surface of the component. The aluminium containing coating may be an aluminide layer, a platinum aluminide layer, a silicon aluminide layer, a chromium aluminide layer or a MCrAlY layer, where M is nickel, cobalt or a combination of nickel and cobalt, Cr is chromium, Al is aluminium and Y is yttrium. Thus, the protective coating, the aluminium containing coating, is on and forms a layer on the surface of the component and the alumina is on and forms a layer on the protective coating, the aluminium containing coating.

Although the present invention has been described with reference to inspecting the whole of the surface of the component, it may alternately be used to inspect the whole of the surface of a particular region of a component.

The invention claimed is:

1. A method of determining the presence of an alumina layer on a surface of a component, an aluminium containing layer being arranged on the surface of the component and an alumina layer being arranged on the aluminium containing layer, the method comprising the steps of:
   a) directly illuminating a surface of a component with radiation at a suitable wavelength to produce excitation of electrons from a normal energy state to a higher energy state in any alumina on the surface of the component,
   b) detecting radiation emitted at a particular wavelength by electrons reverting from the higher energy state to the normal energy state in any alumina on the surface of the component,
   c) analysing the radiation emitted by electrons reverting from the higher energy state to the normal energy state in any alumina on the surface of the component to determine the thickness of the alumina at at least one point on the surface of the component,
   d) comparing the determined thickness of the alumina at the at least one point on the surface of the component with a predetermined thickness of alumina at that point on the surface of the component to decide if the thickness of alumina at the at least one point on the surface of the component is satisfactory.

2. A method as claimed in claim 1 wherein step c) comprises analysing the radiation emitted by electrons reverting from the higher energy state to the normal energy state in any alumina on the surface of the component to determine the thickness of the alumina at a plurality of points on the surface of the component and step d) comprises comparing the determined thickness of the alumina at each of the plurality of points on the surface of the component with a predetermined thickness of alumina at each of the plurality of points on the surface of the component to decide if the thickness of alumina at each of the plurality of points on the surface of the component is satisfactory.

3. A method as claimed in claim 1 wherein step c) comprises analysing the radiation emitted by electrons reverting from the higher energy state to the normal energy state in any alumina on the surface of the component to determine the thickness of the alumina at each point on the surface of the component and step d) comprises comparing the determined thickness of the alumina at each point on the surface of the component with a predetermined thickness of alumina at that point on the surface of the component to decide if the thickness of alumina at each point on the surface of the component is satisfactory.

4. A method as claimed in claim 1 wherein the suitable wavelength is selected from the group consisting of ultraviolet radiation, radiation in the blue region of the radiation spectrum and radiation in the green region of the radiation spectrum.

5. A method as claimed in claim 1 wherein the suitable wavelength is selected from the group consisting of 488 nm, 505 nm, 514 nm and 530 nm.

6. A method as claimed in claim 1 wherein the particular wavelength is in the range of 692 nm to 696 nm.

7. A method as claimed in claim 1 wherein step a) comprises illuminating the surface of the component with radiation from at least one light emitting diode.

8. A method as claimed in claim 1 wherein step b) comprises detecting radiation with a camera.

9. A method as claimed in claim 7 wherein step a) comprises illuminating the surface of the component with radiation from a plurality of light emitting diodes arranged in an array around a camera.

10. A method as claimed in claim 1 wherein step a) comprises illuminating the surface of the component with radiation from at least one laser.

11. A method as claimed in claim 1 wherein the method comprises placing the component in a radiation tight enclosure and illuminating an external surface of the component.

12. A method as claimed in claim 1 wherein the method comprises inserting a baroscope into the component and illuminating an internal surface of the component.

13. A method as claimed in claim 1 wherein the component is a component of a gas turbine engine.

14. A method as claimed in claim 13 wherein the component is a turbine blade or a turbine vane.

15. A method as claimed in claim 1 wherein the aluminium containing layer is an aluminide layer, a platinum aluminide layer, a silicon aluminide layer, a chromium aluminide layer or a MCrAlY layer, where M is nickel, cobalt or a combination of nickel and cobalt, Cr is chromium, Al is aluminium and Y is yttrium.

16. An apparatus for determining the presence of an alumina layer on a surface of a component, an aluminium containing layer being arranged on the surface of the component and an alumina layer being arranged on the aluminium containing layer, the apparatus comprising means to directly illuminate a surface of a component with radiation at a suitable wavelength to produce excitation of electrons from a normal energy state to a higher energy state in any alumina on the surface of the component, means to detect radiation emitted at a particular wavelength by electrons reverting from the higher energy state to the normal energy state in any alumina on the surface of the component, means to analyse the radiation emitted by electrons reverting from the higher energy state to the normal energy state in any alumina on the surface of the component to determine the thickness of the alumina at at least one point on the surface of the component and means to compare the determined thickness of the alumina at the at least one point on the surface of the component with a predetermined thickness of alumina at that point on the surface of the component to decide if the thickness of alumina at the at least one point on the surface of the component is satisfactory.

17. An apparatus as claimed in claim 16 wherein the means to illuminate the surface of the component is arranged to illuminate the surface of the component with ultraviolet radiation, radiation in the blue region and/or radiation in the green region of the radiation spectrum.

18. An apparatus as claimed in claim 16 wherein the means to illuminate the surface of the component is arranged to illuminate the surface of the component with radiation at wavelength selected from the group consisting of 488 nm, 505 nm, 514 nm and 530 nm.

19. An apparatus as claimed in claim 16 wherein the means to detect radiation is arranged to detect radiation at a wavelength in the range of 692 nm to 696 nm.

20. An apparatus as claimed in claim 16 wherein the means to illuminate the surface of the component with radiation is selected from the group consisting of at least one light emitting diode and at least one laser.

21. An apparatus as claimed in claim 16 wherein the means to detect radiation comprises a camera.

22. An apparatus as claimed in claim 20 wherein the means to illuminate the surface of the component comprises a plurality of light emitting diodes arranged in an array around a camera.

23. An apparatus as claimed in claim 21 wherein the camera has a red band-pass filter.

24. An apparatus as claimed in claim 20 wherein the at least one light emitting diode has a filter, the filter is selected from the consisting of a green short-pass filter, a blue filter, an ultraviolet filter and a short pass filter which blocks red light.

25. An apparatus as claimed in claim 16 wherein the apparatus comprises a radiation tight enclosure and the means to illuminate the surface of the component is arranged to illuminate an external surface of the component and the means to illuminate the surface of the component and the means to detect radiation are arranged in the light tight enclosure.

26. An apparatus as claimed in claim 16 wherein the apparatus comprises a boroscope to illuminate an internal surface of the component.

27. A method of determining the presence of an alumina layer on a surface of a component, an aluminum containing layer being arranged on the surface of the component and an alumina layer being arranged on the aluminum containing layer, the method comprising:
  a) directly illuminating a surface of a component with radiation at a suitable wavelength to produce excitation of electrons from a normal energy state to a higher energy state in any alumina on the surface of the component, directly illuminating the surface of the component using an array of light emitting diodes or lasers to inspect the whole of the surface of the component,
  b) detecting radiation emitted at a particular wavelength by electrons reverting from the higher energy state to the normal energy state in any alumina on the surface of the component, the detecting comprising taking a still image of the surface of the component,
  c) analyzing the radiation emitted by electrons reverting from the higher energy state to the normal energy state in any alumina on the surface of the component to determine the thickness of the alumina at each point on the surface of the component, the analyzing comprising analyzing the still image of the surface of the component, and
  d) comparing the determined thickness of the alumina at each point on the surface of the component with a predetermined thickness of alumina at that point on the surface of the component to decide if the thickness of alumina at each point on the surface of the component is satisfactory and hence an aluminum containing layer is present on the surface of the component.

* * * * *